United States Patent
Barbut

(10) Patent No.: US 8,034,043 B1
(45) Date of Patent: Oct. 11, 2011

(54) DEVICES AND METHODS FOR PREVENTING DISTAL EMBOLIZATION USING FLOW REVERSAL BY PARTIAL OCCLUSION OF THE BRACHIOCEPHALIC ARTERY

(75) Inventor: Denise R. Barbut, New York, NY (US)

(73) Assignee: CoAxia, Inc., Maple Grove, MN (US)

( * ) Notice: Subject to any disclaimer, the term of this patent is extended or adjusted under 35 U.S.C. 154(b) by 1967 days.

(21) Appl. No.: 11/020,763

(22) Filed: Dec. 22, 2004

Related U.S. Application Data

(62) Division of application No. 10/614,439, filed on Jul. 2, 2003, now Pat. No. 6,837,881, which is a division of application No. 09/792,600, filed on Feb. 23, 2001, now Pat. No. 6,595,980.

(51) Int. Cl.
*A61M 31/00* (2006.01)
*A61M 29/00* (2006.01)
*A61M 5/00* (2006.01)

(52) U.S. Cl. ............ 604/509; 604/8; 604/9; 604/96.01

(58) Field of Classification Search ............. 604/8–10, 604/96.01, 101.01, 102.02, 101.05, 108, 604/7–510; 623/1.11; 606/108, 191, 192, 606/194
See application file for complete search history.

(56) References Cited

U.S. PATENT DOCUMENTS

| | | | |
|---|---|---|---|
| 4,531,943 A | 7/1985 | Van Tassel et al. | |
| 4,883,459 A | 11/1989 | Calderon | |
| 4,921,478 A | 5/1990 | Solano et al. | |
| 5,423,742 A | 6/1995 | Theron | |
| 5,431,639 A | 7/1995 | Shaw | |
| 5,462,529 A | 10/1995 | Simpson et al. | |
| 5,599,307 A | 2/1997 | Bacher et al. | |
| 5,765,568 A * | 6/1998 | Sweezer et al. | 128/898 |
| 5,769,812 A | 6/1998 | Stevens et al. | |
| 5,833,645 A | 11/1998 | Lieber et al. | |
| 5,833,650 A | 11/1998 | Imran | |
| 5,895,399 A * | 4/1999 | Barbut et al. | 606/159 |
| 5,938,645 A | 8/1999 | Gordon | |
| 5,941,896 A | 8/1999 | Kerr | |
| 6,099,497 A | 8/2000 | Adams et al. | |
| 6,146,370 A * | 11/2000 | Barbut | 604/500 |
| 6,156,005 A | 12/2000 | Theron | |
| 6,161,547 A | 12/2000 | Barbut | |

(Continued)

OTHER PUBLICATIONS

Theron et al., "New Triple Coaxial Catheter System for Carotid Angioplasty with Cerebral Protection," *American Journal of Neuroradiology*, Sep./Oct. 1990, pp. 869-874, vol. 11, American Society of Neuroradiology, USA.

(Continued)

*Primary Examiner* — Leslie Deak
*Assistant Examiner* — Philip Wiest
(74) *Attorney, Agent, or Firm* — O'Melveny & Myers LLP

(57) ABSTRACT

The invention provides a medical device having a catheter and one or more expandable constricting/occluding members. The catheter is adapted for use with therapeutic or diagnostic devices, including an angioplasty/stent catheter and an atherectomy catheter. The constrictor/occluder is mounted at the distal end of the catheter. Manometers may be mounted distal to one or more constrictors for measuring pressure distal to the constrictor(s). Methods of using the devices for preventing distal embolization during extracranial or intracranial carotid procedures or vertebral artery procedures by reversing blood flow in an internal carotid artery, an external carotid artery, and/or a common carotid artery toward the subclavian artery are disclosed.

12 Claims, 18 Drawing Sheets

U.S. PATENT DOCUMENTS

| | | | |
|---|---|---|---|
| 6,165,199 | A | 12/2000 | Barbut |
| 6,168,579 | B1 | 1/2001 | Tsugita |
| 6,206,868 | B1 | 3/2001 | Parodi |
| 6,312,444 | B1 * | 11/2001 | Barbut .......................... 606/200 |
| 6,383,172 | B1 | 5/2002 | Barbut |
| 6,413,235 | B1 | 7/2002 | Parodi |
| 6,454,741 | B1 | 9/2002 | Muni et al. |
| 6,508,777 | B1 | 1/2003 | Macoviak et al. |
| 6,676,683 | B1 | 1/2004 | Addis |
| 7,635,376 | B2 * | 12/2009 | Barbut .......................... 606/194 |

OTHER PUBLICATIONS

Jochem et al., "Radiographic Anatomy of the Coronary Collateral Circulation," *Anatomy of Coronary Collaterals*, Sep. 1972, pp. 50-60.

* cited by examiner

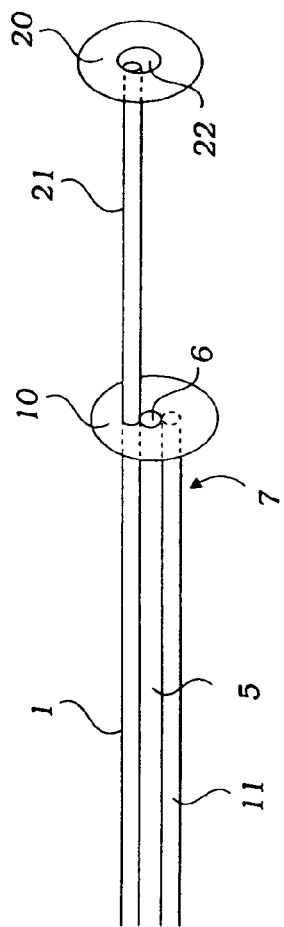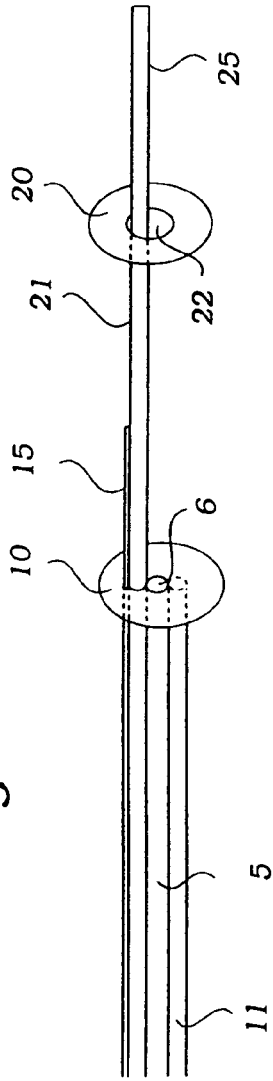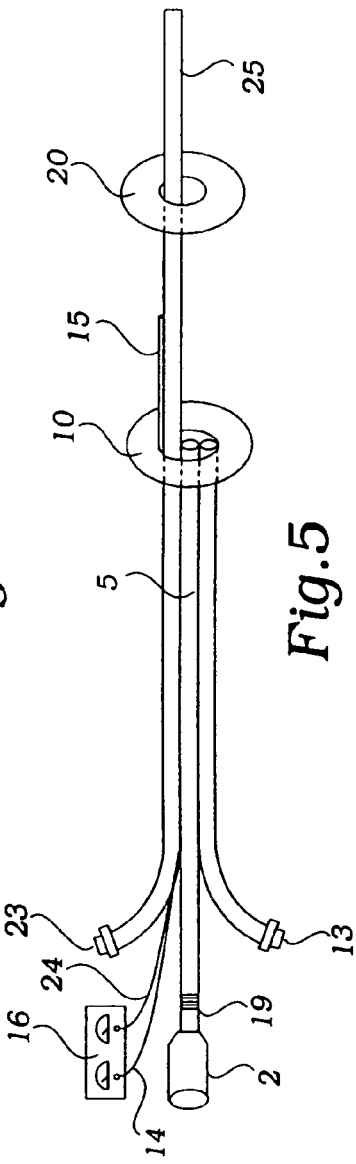

DEVICES AND METHODS FOR PREVENTING DISTAL EMBOLIZATION USING FLOW REVERSAL BY PARTIAL OCCLUSION OF THE BRACHIOCEPHALIC ARTERY

This is a divisional of U.S. application Ser. No. 10/614,439, filed Jul. 2, 2003 now U.S. Pat. No. 6,837,881, which is a divisional of U.S. application Ser. No. 09/792,600, filed Feb. 23, 2001, now U.S. Pat. No. 6,595,980, both of which are incorporated herein by reference in their entirety.

FIELD OF THE INVENTION

The present invention relates generally to devices and methods useful in treating patients with stroke or occlusive cerebrovascular disease. More specifically, the invention provides an extracranial device capable of reversing flow down a vertebral artery, an internal carotid artery, an external carotid artery and/or a common carotid artery, and into the subclavian artery during an invasive procedure, thereby avoiding distal embolization of vascular debris. Various diagnostic or therapeutic instruments, including an atherectomy catheter, a filter, and/or an angioplasty/stent catheter, can be introduced through the device for treating the occlusion. The invention may also be useful to reverse flow and pull back embolic debris during a stroke.

BACKGROUND OF THE INVENTION

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. When a patient presents neurological symptoms and signs that resolve completely within 1 hour, the term transient ischemic attack (TIA) is used. Etiologically, TIA and stroke share the same pathophysiologic mechanisms and thus represent a continuum based on persistence of symptoms and extent of ischemic insult.

Outcome following stroke is influenced by a number of factors, the most important being the nature and severity of the resulting neurologic deficit. Overall, less than 80% of patients with stroke survive for at least 1 month, and approximately 35% have been cited for the 10-year survival rates. Of patients who survive the acute period, up to 75% regain independent function, while approximately 15% require institutional care.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are hemispheric ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. The extracranial or intracranial internal carotid artery, commonly affected by atherosclerosis causing symptomatic occlusion in the arterial lumen, is often responsible for hemispheric ischemic stroke and generating thromboembolic material downstream to the distal cerebral vessels. Treatment of the occluded carotid artery in patients with stroke and TIA or for stroke prevention inpatients with asymptomatic flow limiting carotid stenosis includes performing angioplasty, stent placement, or atherectomy on the occluded carotid artery. This is also true of the vertebral artery. Unfortunately, placing instrumentation within a diseased artery is associated with increased risk of ischemic stroke, since manipulation of an atheromatous plaque in the arterial wall often causes emboli to dislodge distally in the narrow cerebral arteries.

Current methods of preventing distal embolization from carotid instrumentation include insertion of a blood filter distal to the occlusion and suctioning embolic debris during the procedures. Disadvantages associated with the conventional methods are that (1) inserting the filter through the atheromatous lesion is associated with increased risk of distal embolization, (2) using suction to reverse the flow in the internal carotid artery may increase a patient's blood loss if the suctioned blood is discarded, and (3) systemic anticoagulation and pumping may be required to recycle the suctioned blood back into the arterial or venous system, and such anticoagulation is associated with increased risk of hemorrhage.

New devices and methods are thus needed for patients undergoing carotid procedures for definitive or prophylactic treatment of carotid plaque, which minimize the risk of distal embolization and prevent ischemic stroke.

SUMMARY OF THE INVENTION

The invention provides devices and methods for preventing ischemic stroke in patients undergoing percutaneous invasive vertebral or carotid procedures, including angioplasty, stent placement, and/or filter insertion, by reversing blood flow down a vertebral artery, an extracranial or intracranial internal carotid artery, an external carotid artery, and/or a common carotid artery and into the ipsilateral subclavian artery. In this way, embolic debris generated as a result of placing instrumentation within a diseased artery is diverted to the subclavian artery, thereby preventing stroke by minimizing distal embolization to the narrow cerebral vessels. The devices and methods are also useful to remove an embolus and improve flow (by reversing collateral blood flow across the circle of Willis) in patients with acute stroke.

The invention utilizes devices comprising a catheter having one or two expandable constricting members at its distal end. Each constrictor may be a balloon, in certain cases a toroidal balloon, or a device of any other appropriate shape, so that it can fully or partially occlude blood flow. The lumen of the catheter may be adapted for insertion of a therapeutic instrument, such as an angioplasty, atherectomy, and/or stent catheter. A manometer is optionally mounted proximal and/or distal to the constricting member for monitoring blood pressure proximal and/or distal the constrictor.

The occluder/constrictor is mounted near the distal end of the catheter, in certain cases proximal to a port. Each balloon occluder and constrictor communicates with an inflation lumen and an inflation port at the proximal end of the catheter. In certain embodiments, the catheter will include first and second constriction/occlusion members. The second constrictor is mounted on a second member that is slideably insertable through the catheter, and passes beyond the first constrictor. In this way, the second member and the second constrictor are moveable longitudinally relative to the first constrictor. In other embodiments, the constrictor may consist of a balloon having more than one opening at its center for the passage of blood, or may consist of more than one expandable balloons allowing passage of blood through the gap between the arterial wall and the expanded balloons. The proximal end of the catheter may include a hemostatic valve.

In still another embodiment, the catheter includes a second lumen communicating with a proximal end and an infusion port at its distal end. The port is located distal to the distal port of the catheter. The second lumen and its port are adapted for delivering a pharmaceutical agent to the carotid, brachiocephalic and/or subclavian arteries, including an angiographic dye. Any device described in Barbut, U.S. Pat. No. 6,146,370, incorporated herein by reference in its entirety, may also be used in the methods described herein.

The invention provides methods for reversing flow in a vertebral or carotid artery having an atheromatous lesion. More specifically, the methods are useful in reversing flow down a vertebral artery, an extracranial or intracranial internal carotid artery, an external carotid artery, and/or a common carotid artery and into the subclavian artery. In a first method, using the devices described above, the distal end of the catheter is inserted into the right brachiocephalic artery. The catheter can be inserted over a guidewire through an incision on a peripheral artery, including the femoral artery, the subclavian artery, or the brachiocephalic artery. The catheter is positioned to locate the constricting member within the right brachiocephalic artery. Preferably, the constrictor is expanded to completely or partially occlude the right brachiocephalic artery. At a critically low brachiocephalic pressure distal to the constriction, blood flow in the carotid and vertebral arteries is reversed to pass over the atheromatous lesion and into the right subclavian artery. The flow reversal can be verified fluoroscopically with dye. If flow reversal fails to occur or if augmentation of flow reversal is desired, a second constricting member is expanded in the right subclavian artery, further reducing the pressure in the subclavian artery to facilitate reversal of flow down the carotid artery and into the subclavian artery.

In another method, the distal end of the catheter is inserted into the aorta in the takeoff of the left common carotid artery and left subclavian artery. The catheter is positioned to locate the constricting member within the inlet of the left subclavian artery and the left common carotid artery. The constrictor is expanded to completely or partially occlude the subclavian and common carotid artery. At a critically low pressure, blood flow in the carotid artery is reversed to pass over the atheromatous lesion and into the left subclavian artery. The flow reversal can be verified fluoroscopically with dye. If flow reversal fails to occur or if augmentation of flow reversal is desired, a second constricting member is expanded in the left subclavian artery, further reducing the pressure in the subclavian artery to facilitate reversal of flow down the carotid artery and into the subclavian artery.

In another method, using the device having a second occluder including a shunt for the passage of blood therethrough, the catheter is inserted in the right brachiocephalic artery, with the first occluder located in the right brachiocephalic artery and the second occluder located in the right subclavian artery. Preferably, the first occluder is expanded to occlude the brachiocephalic artery followed by expansion of the second occluder to occlude the subclavian artery. Alternatively, the second occluder is expanded to occlude the subclavian artery followed by expansion of the first occluder to occlude the brachiocephalic artery.

After blood reversal is confirmed, procedures on either the vertebral artery, the internal carotid artery or branches thereof (e.g., MCA or ACA), external carotid artery, or common carotid artery can be performed by advancing a therapeutic or diagnostic instrument through the lumen and port of the catheter distal to the occluder. An atherectomy catheter, for example, can be introduced to remove the atheroma in the right internal carotid artery without fear of distal embolization.

It will be understood that there are several advantages in using the devices and methods disclosed herein for prevention of distal embolization during use of instrumentation in the carotid arteries. For example, the devices (1) abolish the need for suction distal to the constricting/occluding member, thereby minimizing blood loss, (2) eliminate the need for systemic anticoagulation, pumping, and a second arterial or venous stick, all of which are required where suction is employed, (3) can be used to introduce a variety of diagnostic or therapeutic instrument to the carotid artery, (4) can be used in any procedures which require instrumentation within the carotid artery, (5) can be used for definitive treatment of acute or subacute ischemic stroke, (6) can be used in the angiogram or fluoroscopy suite available in most hospitals, (7) require only one incision site for entry, and (8) can be used to perform an interventional procedure without distal protection (e.g., a distal filter), and without crossing the lesion.

BRIEF DESCRIPTION OF THE DRAWINGS

FIG. 4A depicts a distal region of another embodiment of the medical device having a constricting member distal an occluding member.

FIG. 4B depicts a distal region of another embodiment of the device having two manometers.

FIG. 5 depicts the device of FIG. 4B including a hemostatic valve at its proximal end.

DETAILED DESCRIPTION

The cerebral circulation is regulated in such a way that a constant total cerebral blood flow (CBF) is generally maintained under varying conditions. For example, a reduction in flow to one part of the brain, such as in stroke, may be compensated by an increase in flow to another part, so that CBF to any one region of the brain remains unchanged. More importantly, when one part of the brain becomes ischemic due to a vascular occlusion, the brain compensates by increasing blood flow to the ischemic area through its collateral circulation via the Circle of Willis.

Figure 1:
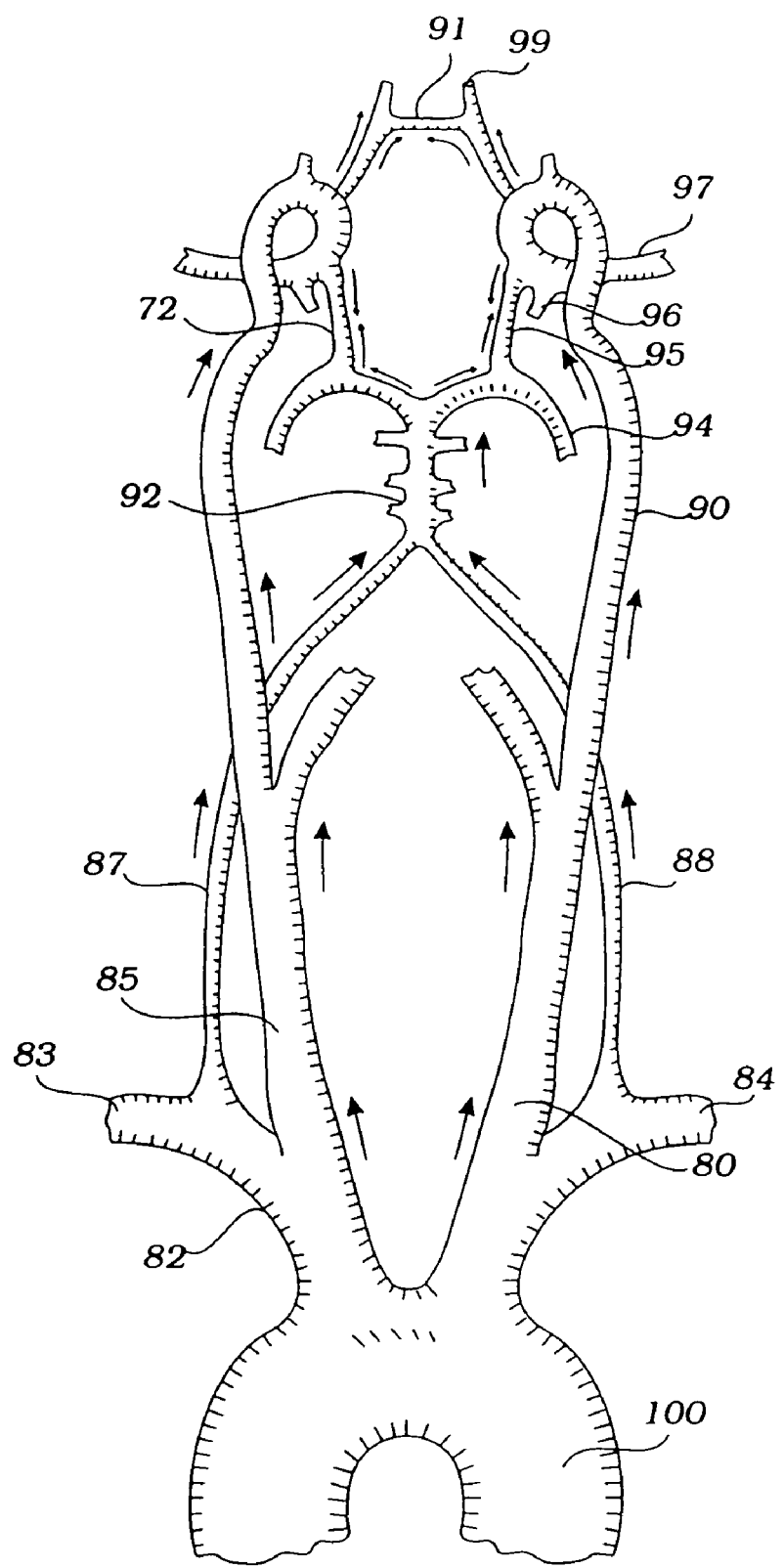
FIG. 1 depicts normal cerebral circulation in the Circle of Willis.

FIG. 1 depicts a normal cerebral circulation and formation of Circle of Willis. Aorta 100 gives rise to right brachiocephalic trunk 82, left common carotid artery (CCA) 80, and left subclavian artery 84. The brachiocephalic artery further branches into right common carotid artery 85 and right subclavian artery 83. The left CCA gives rise to left internal carotid artery (ICA) 90 which becomes left middle cerebral artery (MCA) 97 and left anterior cerebral artery (ACA) 99. Anteriorly, the Circle of Willis is formed by the internal carotid arteries, the anterior cerebral arteries, and anterior communicating artery 91 which connects the two ACAS. The right and left ICA also send right posterior communicating artery 72 and left posterior communicating artery 95 to connect respectively with right posterior cerebral artery (PCA) 74 and left PCA 94. The two posterior communicating arteries and PCAs, and the origin of the posterior cerebral from basilar artery 92 complete the circle posteriorly. The left CCA also gives rise to external carotid artery (ECA) 78, which branches extensively to supply most of the structures of the head except the brain and the contents of the orbit. The ECA also helps supply structures in the neck.

Figure 2:
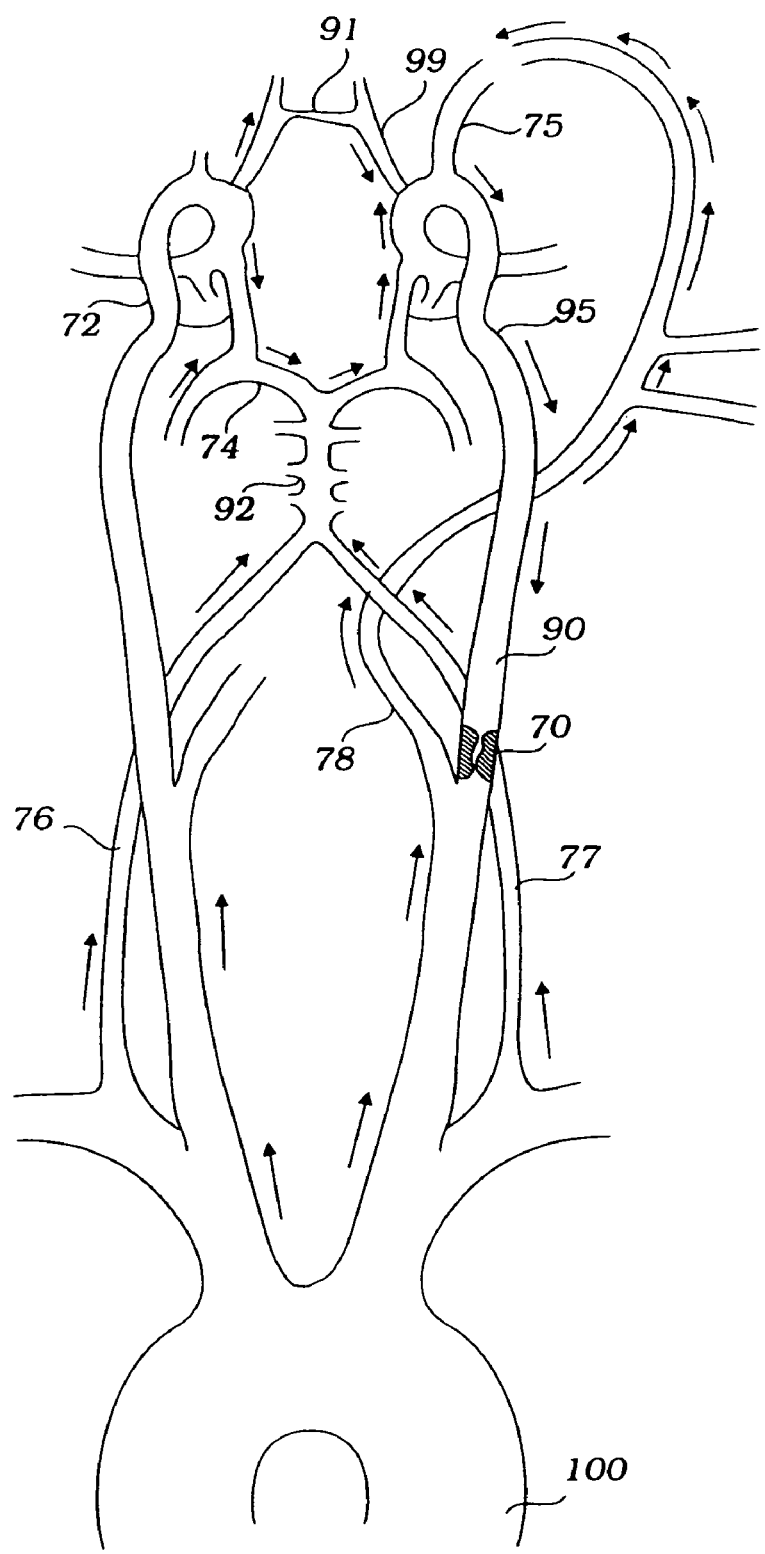
FIG. 2 depicts a reversed circulation in the Circle of Willis to compensate for an occlusion in the left internal carotid artery.

When occluding lesion 70 occurs acutely, for example, in left internal carotid artery 90, as depicted in FIG. 2, blood flow in the right cerebral arteries, left external carotid artery 78, right vertebral artery 76, and left vertebral artery 77 increases, resulting in a directional change of flow through the Circle of Willis to compensate for the sudden decrease of blood flow in the left internal carotid artery. Specifically, blood flow reverses in right posterior communicating artery 72, right PCA 74, and left posterior communicating artery 95. Anterior communicating artery 91 opens, reversing flow in left ACA 99, and flow increases in the left external carotid artery, reversing flow along left ophthalmic artery 75, all of which contribute to flow in left ICA 90 distal to the occluding lesion.

Figure 3A:
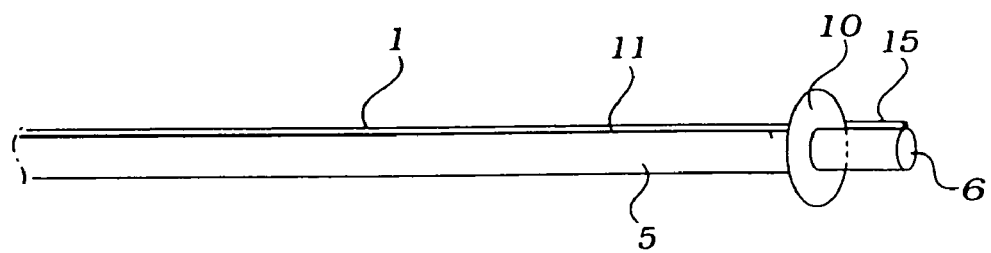
FIG. 3A depicts a distal region of an embodiment of the medical device having an occluding member for prevention of acute stroke during use of instrumentation in a carotid artery.

Balloon catheters for achieving flow reversal in carotid arteries were described in Barbut, U.S. Pat. No. 6,146,370, incorporated herein by reference in its entirety. FIG. 3A depicts one embodiment of the device for preventing distal embolization during use of carotid instrumentation. The device comprises catheter 1 and balloon occluder 10. The catheter has lumen 5 communicating with a proximal end and port 6 at a distal end. The lumen and port are adapted for introduction of therapeutic or diagnostic instruments, e.g., an atherectomy catheter, angioplasty catheter, and stent, to a carotid artery. Balloon occluder 10, communicating with inflation lumen 11, is mounted on the distal end of the catheter proximal to port 6. Manometer 15 is mounted distal to occluder 10 for monitoring blood pressure downstream the occluder.

Figure 3B:
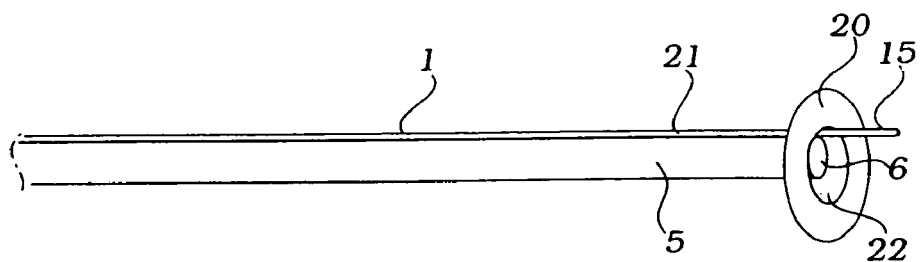
FIG. 3B depicts a distal region of another embodiment of the medical device having a constricting member.

FIG. 3B depicts another embodiment of the device having constricting member 20 mounted on a distal region of the catheter proximal to port 6. Constricting member 20 communicates with inflation lumen 21. The constrictor has central opening 22 that allows passage of blood. Manometer 15 is mounted distal to constrictor 20 for monitoring blood pressure downstream the constrictor.

FIG. 4A depicts another embodiment of the device comprising catheter 1, balloon occluder 10, and constrictor 20. Lumen 5 of the catheter communicates with port 6 at distal end 7. The lumen and port are adapted for introduction of therapeutic or diagnostic instruments. Balloon occluder 10, communicating with inflation lumen 11, is mounted on the distal end of the catheter proximal to port 6. Balloon constrictor 20, communicating with inflation lumen 21, is mounted distal to port 6 and first occluder 10. The constrictor has central opening 22 that allows passage of blood. Inflation lumen 21 is an elongate member which, in certain embodiments, is slidably inserted through catheter 1, and is moveable longitudinally relative to catheter 1 and occluder 10.

FIG. 4B depicts another embodiment of the device having two manometers. Manometer 15 is mounted distal to occluder 10 for measuring blood pressure between the occluder and the constrictor. Manometer 25 is mounted distal to constrictor 20 for measuring blood pressure downstream from constrictor 20. Any of the manometers of any device described herein will be understood to include a tube communicating with a pressure gauge at the proximal end of the catheter.

In FIG. 5, proximal ends 14 and 24 of respective manometers 15 and 25 are connected to pressure monitor 16 for measuring blood pressure proximal and distal the constrictor. Inflation ports 13 and 23 communicate, respectively, with inflation lumens 11 and 21 for expanding balloon occluder 10 and constrictor 20. Lumen 5 of the catheter communicates with proximal end 2, which includes hemostatic valve 19.

Figure 5A:
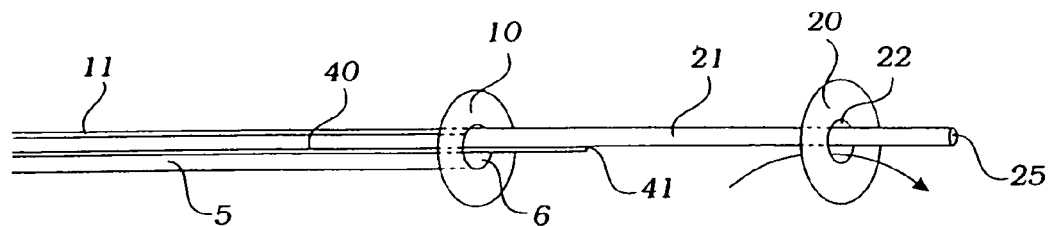
FIG. 5A depicts another embodiment of the device having a proximal occluder and a distal constrictor.
Figure 5B:
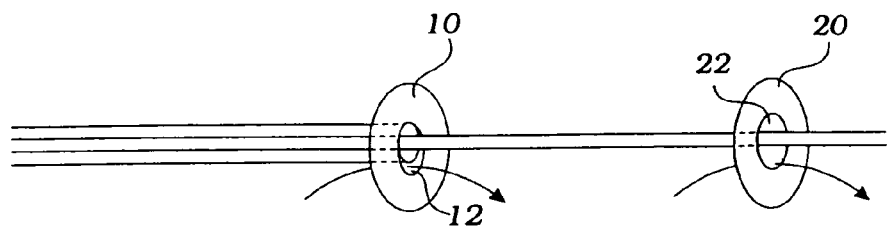
FIG. 5B depicts another embodiment of the device having a proximal constrictor and a distal constrictor.
Figure 5C:
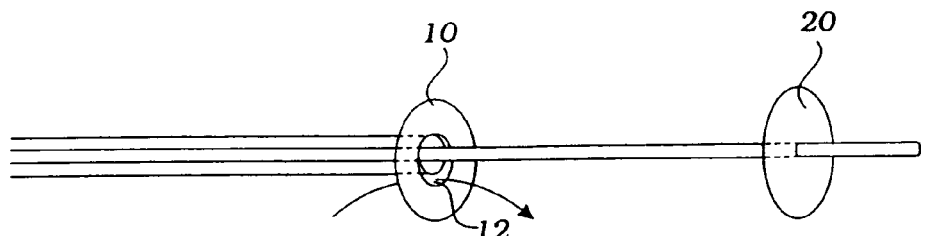
FIG. 5C depicts another embodiment of the device having a proximal occluder and a distal occluder.
Figure 5D:
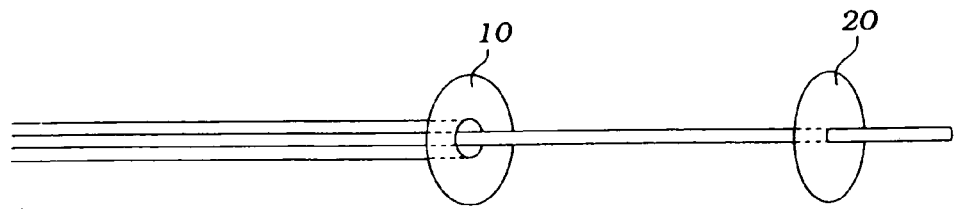
FIG. 5D depicts another embodiment of the device having a proximal occluder and a distal occluder.

FIGS. 5A, 513, 5C, and 5D depict alternative devices for use in the inventions described herein. Each catheter has first balloon 10 and second balloon 20. All combinations of constrictors and occluders are contemplated. Thus, first balloon 10 may be an occluder, and second balloon 20 may be a constrictor (FIG. 5A). Alternatively, first balloon 10 may be a constrictor, and second balloon 20 may be a constrictor (FIG. 5B). Alternatively, first balloon 10 may be a constrictor, and second balloon 20 may be an occluder (FIG. 5C). Alternatively, first balloon 10 may be an occluder, and second balloon 20 may be an occluder (FIG. 5D).

Figure 6A:
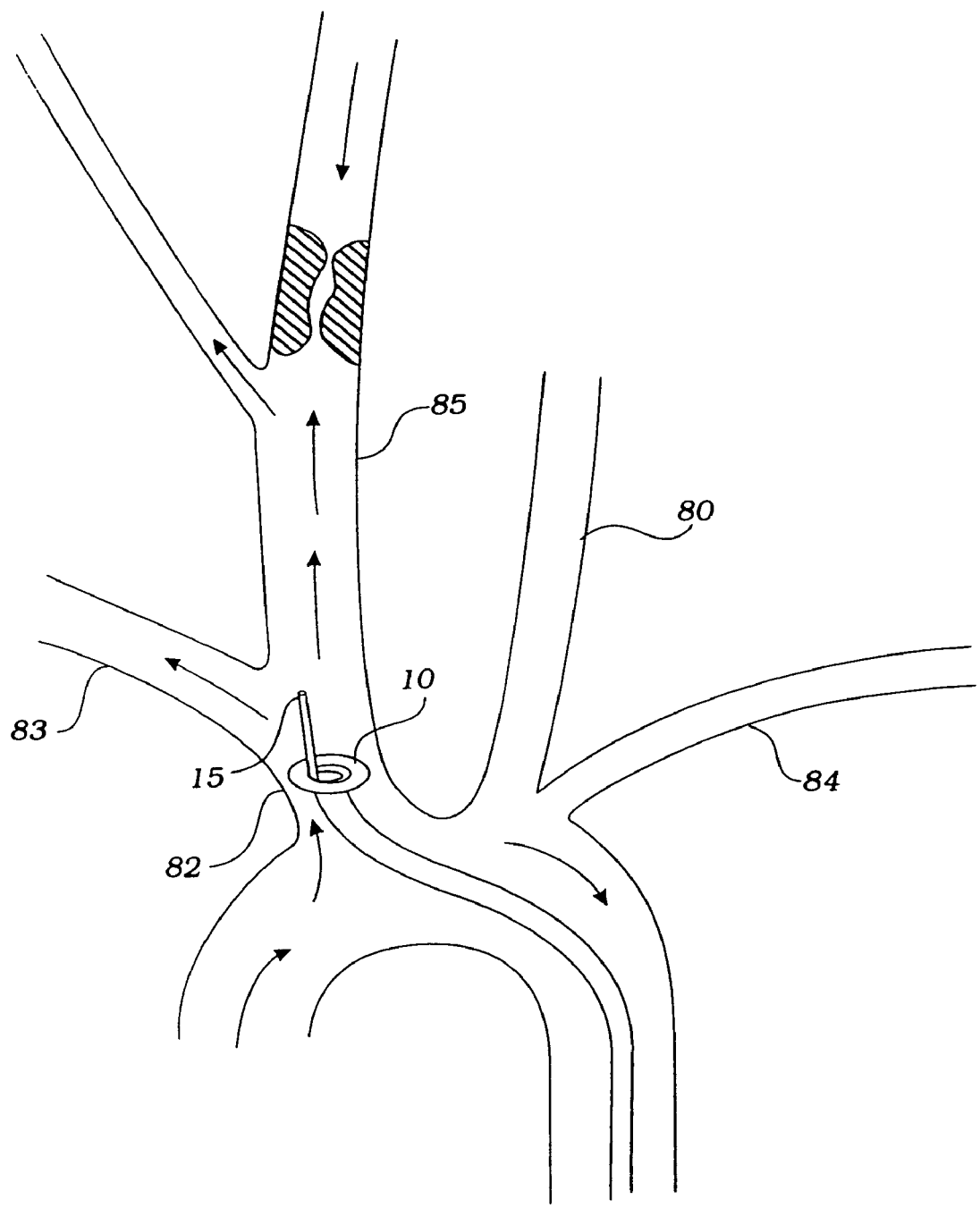
FIG. 6A depicts the device of FIG. 3A inserted in the right brachiocephalic artery.

In using the device of FIG. 3A to treat an occluding lesion in the right internal carotid artery, for example, a percutaneous incision is first made on a peripheral artery, such as the femoral artery. A guidewire is inserted through the incision into the right brachiocephalic artery in an antegrade direction. Alternatively, the guidewire is inserted into the right brachiocephalic artery from an incision in the left subclavian artery or left brachial artery in a retrograde direction, or in a retrograde direction through the right subclavian artery. The distal end of the catheter is inserted over the guidewire, so that occluder 10 is positioned in right brachiocephalic artery 82 as shown in FIG. 6A; where needed, a guiding catheter can also be used. The guidewire is then removed from the catheter.

Figure 6B:
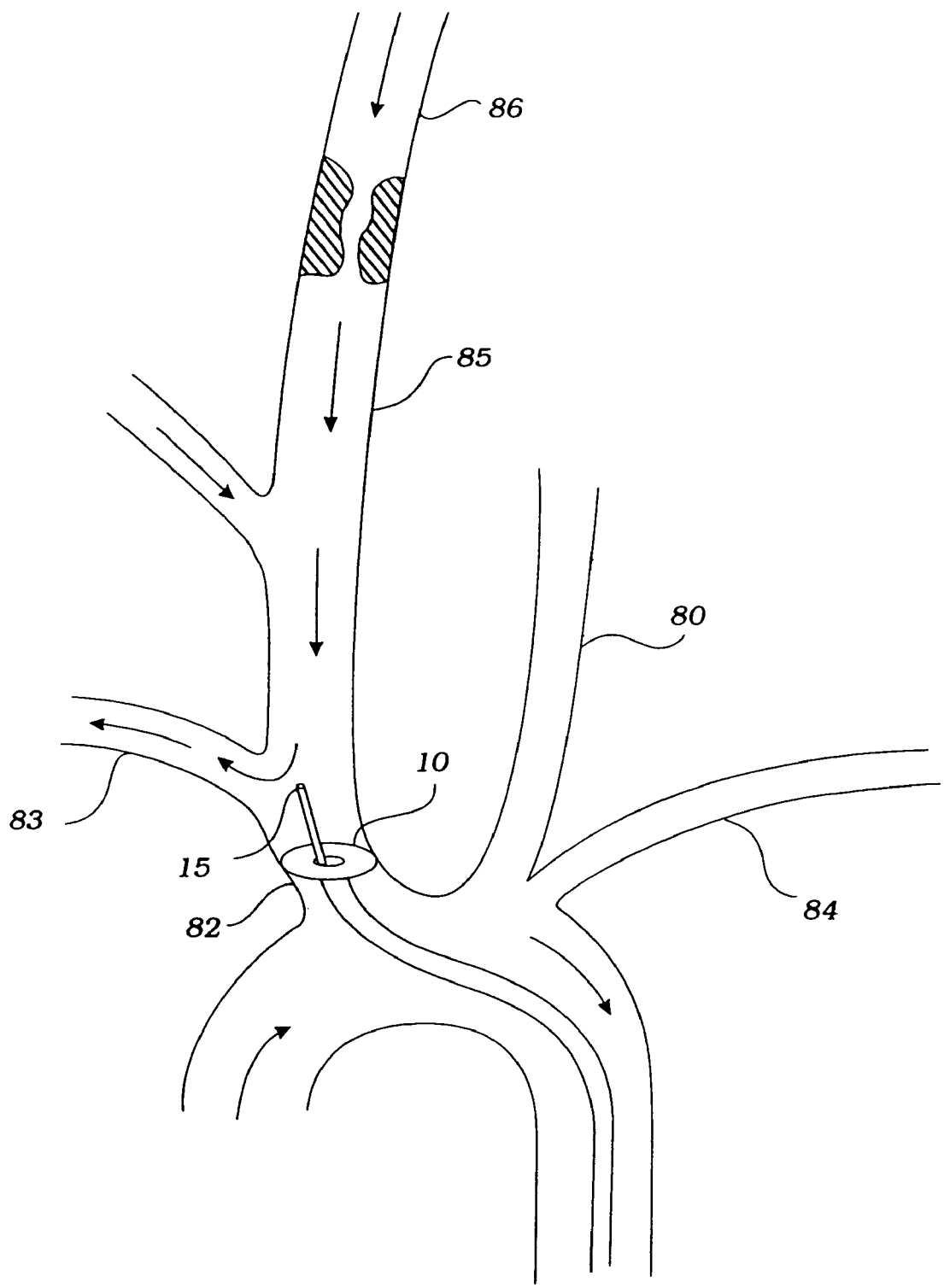
FIG. 6B depicts the expanded occluder causing reversal of blood flow from the internal carotid artery to the subclavian artery.

Occluder 10 is slowly expanded to constrict right brachiocephalic artery 82, causing progressive decline in right brachiocephalic and CCA pressure as shown in FIG. 6B. The pressure in right brachiocephalic artery 82 distal to occluder 10 can be measured by manometer 15. At a critically low pressure in the brachiocephalic artery, blood flow in right ICA 86 and CCA 85 reverses down toward the brachiocephalic artery and into right subclavian artery 83. The reversal of blood flow down the CCA and up the subclavian artery can be verified fluoroscopically with dye.

Figure 6C:
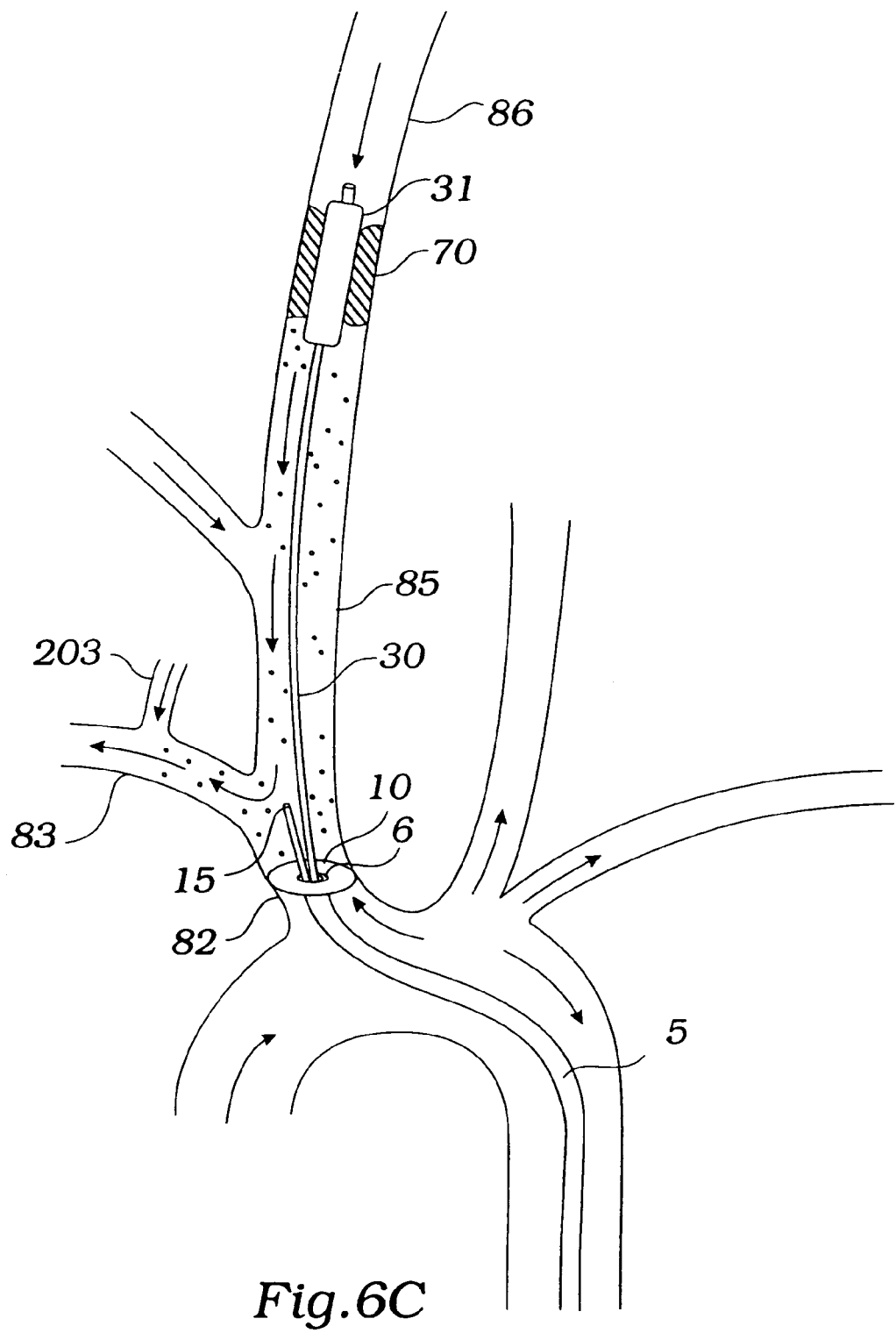
FIG. 6C depicts an angioplasty balloon catheter inserted through the device in FIG. 6B to treat an occluding lesion in the right internal carotid artery.
Figure 6D:
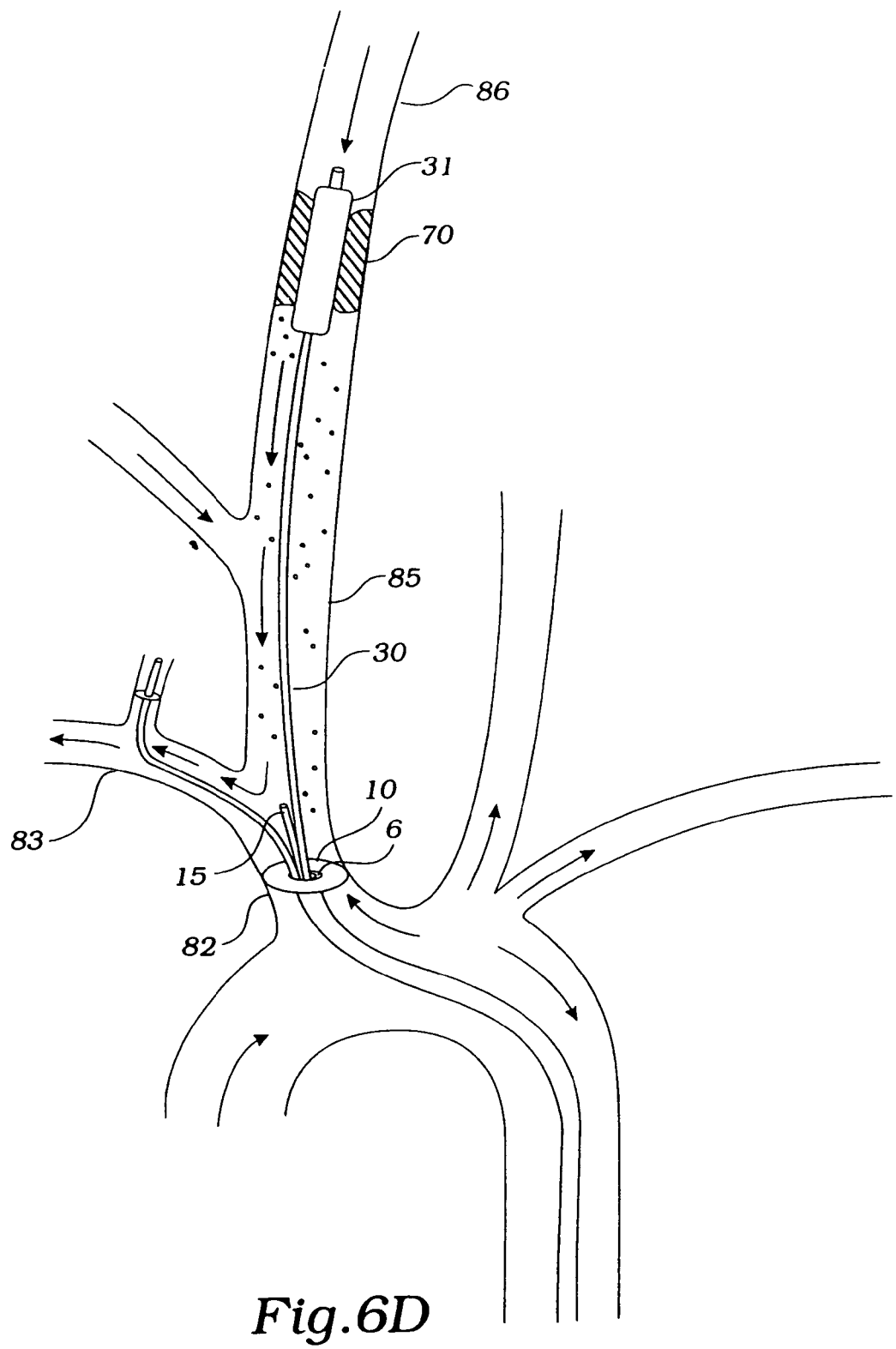
FIG. 6D depicts the use of an occluder to establish carotid flow reversal and a second balloon to protect the vertebral artery against embolization.

After blood reversal is established from the CCA to the subclavian artery, the devices and methods described above can be used in any carotid procedures. For example, in FIG. 6C, interventional catheter 30 carrying angioplasty balloon 31 is introduced through lumen 5 and port 6 of the device. The angioplasty balloon is shown expanding over atheromatous lesion 70 in right ICA 86, thereby compressing the lesion and enlarging the lumenal diameter. Compression of the atheroma by the angioplasty balloon often generates embolic debris, including calcium, atheromatous plaque, and thrombi. With reversal of blood flow from the ICA to the CCA and into the right subclavian artery, distal embolization to the intracranial cerebral arteries is avoided, thereby minimizing risk of ischemic stroke. Distal embolization of the branches of the subclavian artery has far less devastating consequences than the ICA. Blood flow through the affected subclavian artery and its branches is reduced but not abolished due to collateral circulation. For example, collateral flow is established from right vertebral artery 203 into right subclavian artery 83, and this flow reversal in the vertebral artery protects against infarction in the posterior circulation, including the brain stem. In the event that flow reversal does not occur in the vertebral artery upon brachiocephalic occlusion, second balloon 204 (see FIG. 6D) is positioned within the takeoff to the vertebral artery to protect against infarction in the posterior circulation.

Figure 7A:
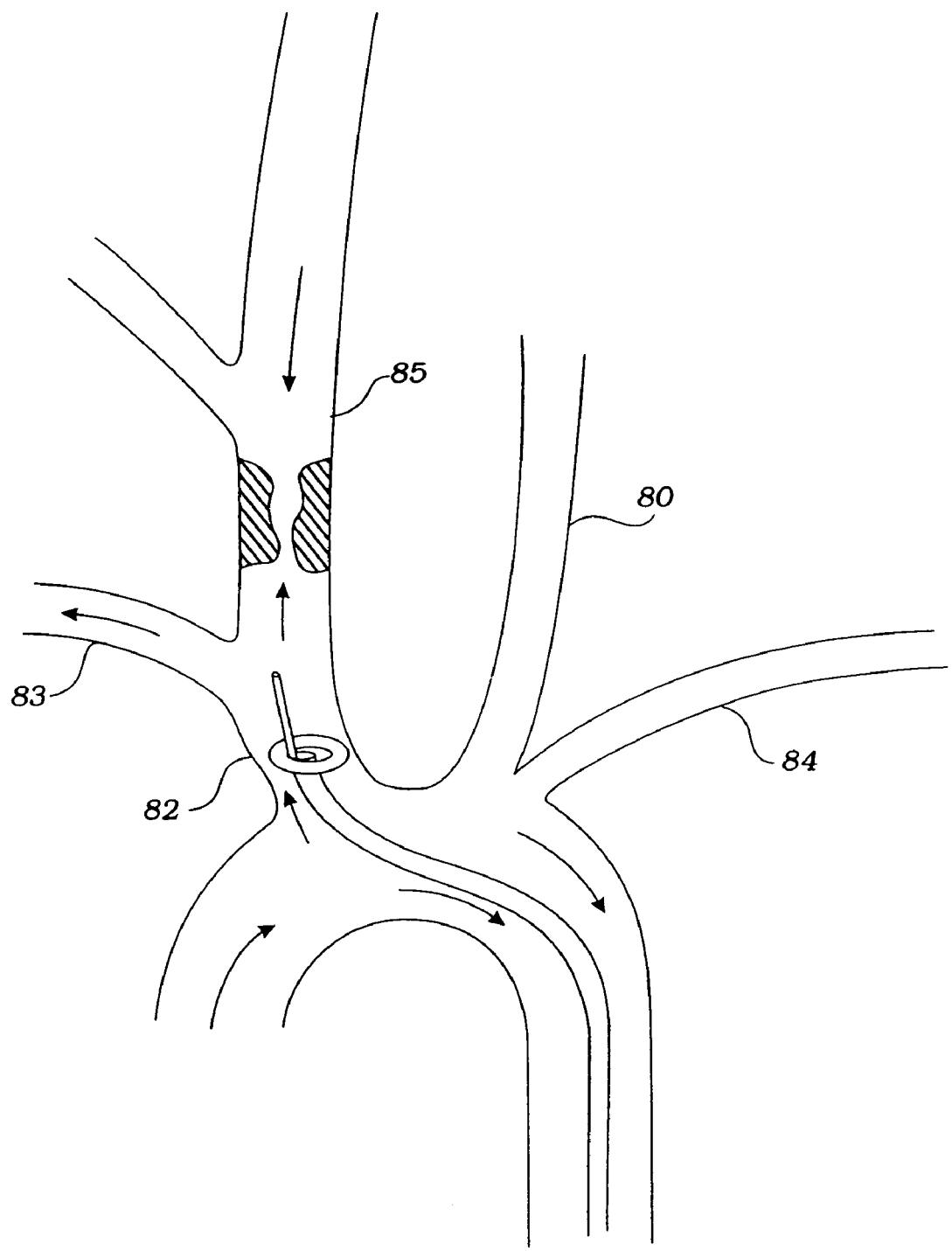
FIG. 7A depicts the device of FIG. 3B inserted in the right brachiocephalic artery.
Figure 7B:
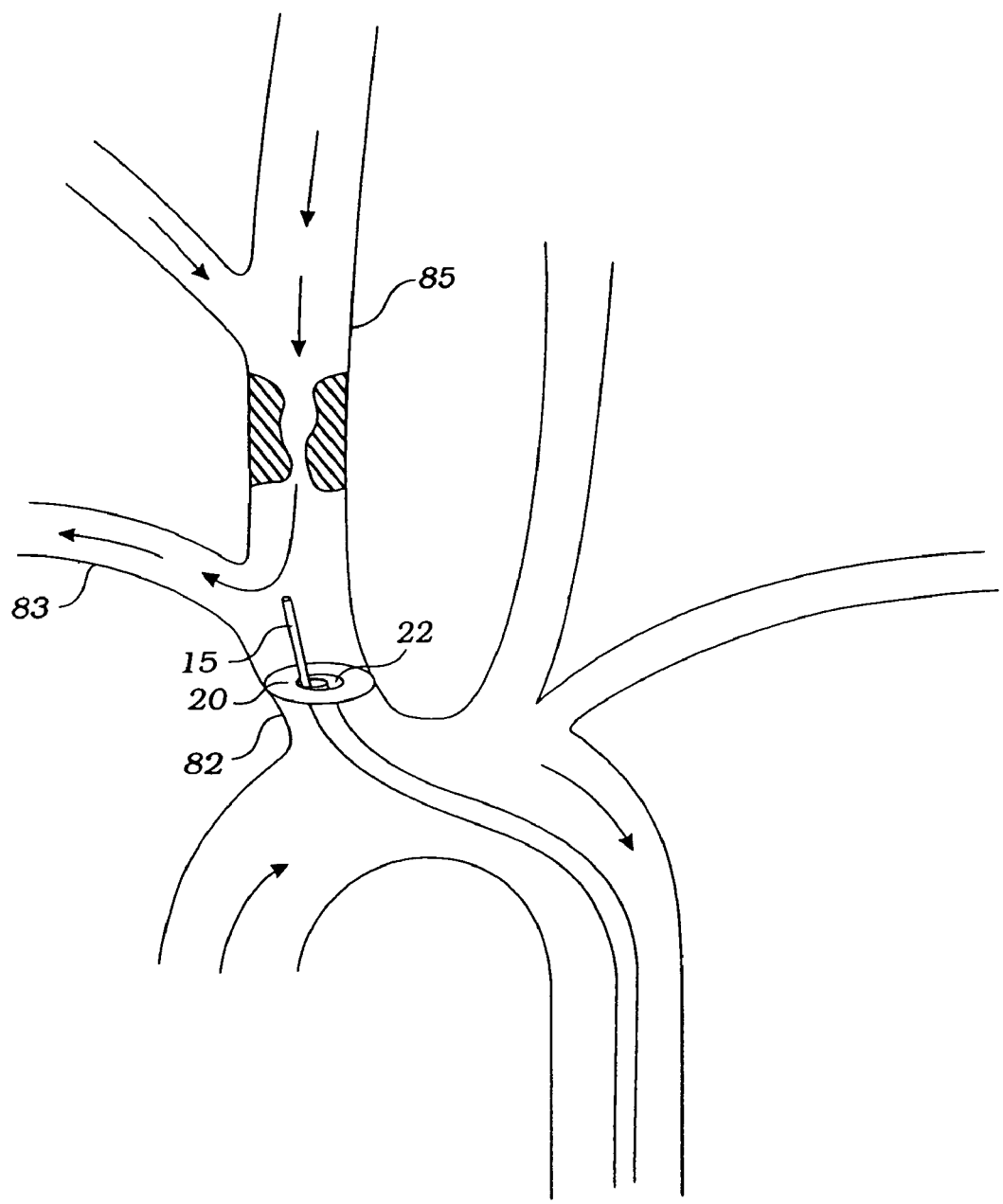
FIG. 7B depicts the expanded constricting member causing reversal of blood flow from the common carotid artery to the subclavian artery.
Figure 7C:
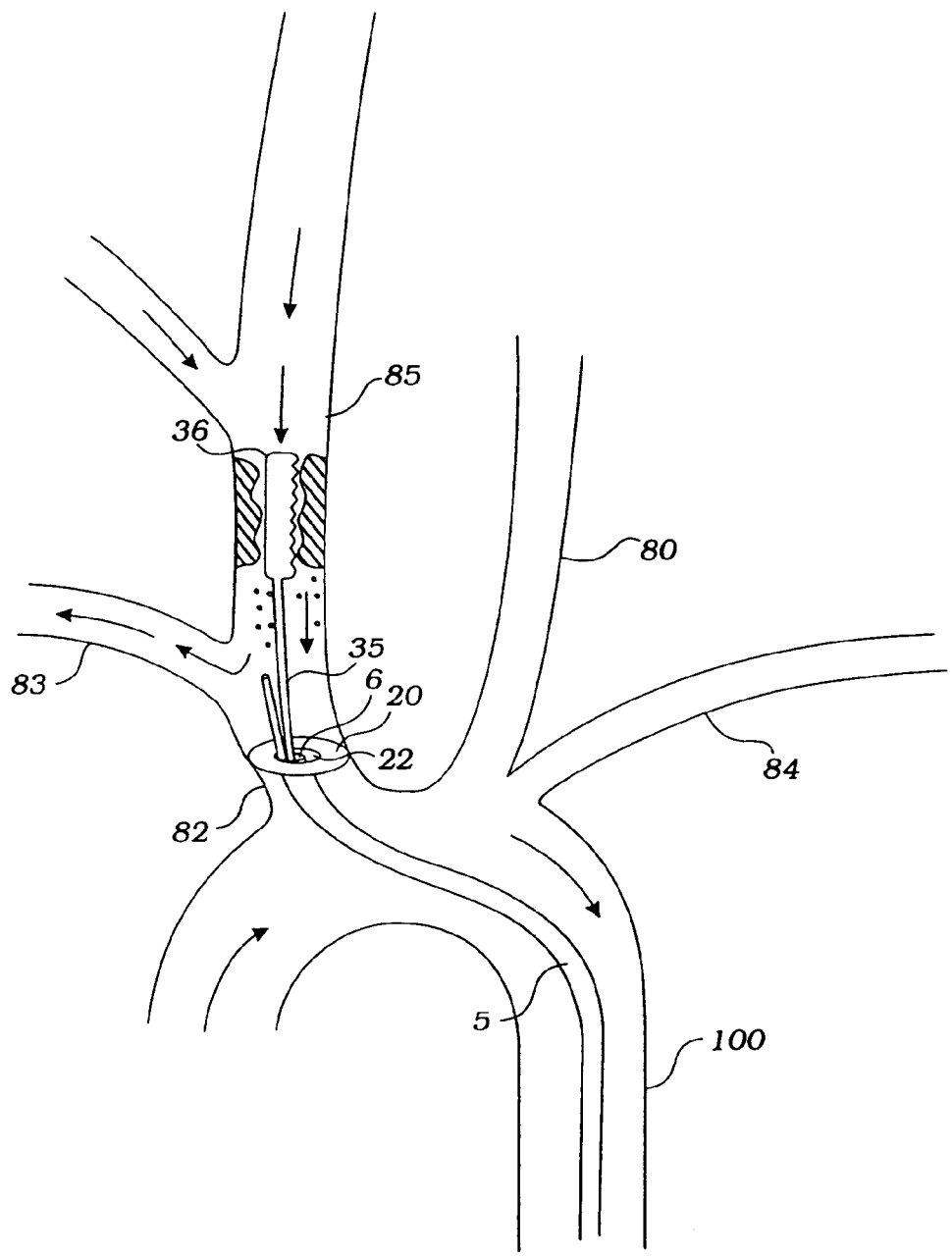
FIG. 7C depicts an atherectomy catheter inserted through the device in FIG. 7B to treat an occluding lesion in the right common carotid artery.

In using the device of FIG. 3B to treat an occluding lesion in the right common carotid artery, for example, the distal end of the device is first inserted into right brachiocephalic artery 82 as shown in FIG. 7A. Constricting member 22 is then expanded to constrict the lumen of the brachiocephalic artery, causing reversal of blood flow from right CCA 85 toward brachiocephalic artery 82 and into right subclavian artery 83 as shown in FIG. 7B. After reversal of blood flow is verified angiographically, a therapeutic instrument, such as an atherectomy catheter as depicted in FIG. 7C, is inserted through lumen 5 and port 6 to treat the occluding lesion. Embolic debris generated during the procedure is diverted from CCA 85 toward subclavian artery 83, thereby preventing distal cerebral embolization and ischemic stroke. The construction of atherectomy catheters is well known in the art and will not be repeated in detail here. The reader is referred instead to Fischell, U.S. Pat. No. 5,409,454; Fischell, U.S. Pat. No. 4,898,575; Rydell, U.S. Pat. No. 4,857,045; Yock, U.S. Pat. Nos. 4,794,931, 5,000,185, and 5,313,949; Jang et al., U.S. Pat. No. 5,507,292; Farr, U.S. Pat. Nos. 4,950,277, 4,986,807, 5,019,088; Shiber, U.S. Pat. Nos. 4,894,051, 4,957,482, 4,979,939, 5,007,896, 5,024,651, 5,135,531; Summers, U.S. Pat. No. 5,087,265; Plassche et al., U.S. Pat. No. 5,318,576; Belknap, U.S. Pat. No. 5,366,464; Jang et al., U.S. Pat. No. 5,402,790; Mazur et al., Catherization and Cardiovascular Diagnosis 31:79-84 (1994); Fischell et al., U.S. Pat. Nos. 4,886,061, 5,100,425; and Barbut et al., U.S. Pat. No. 5,662,671, all of which are incorporated herein by reference as if fully set forth herein. In other embodiments, catheter 35 may carry angioplasty balloon 36 or a stent.

Figure 8:
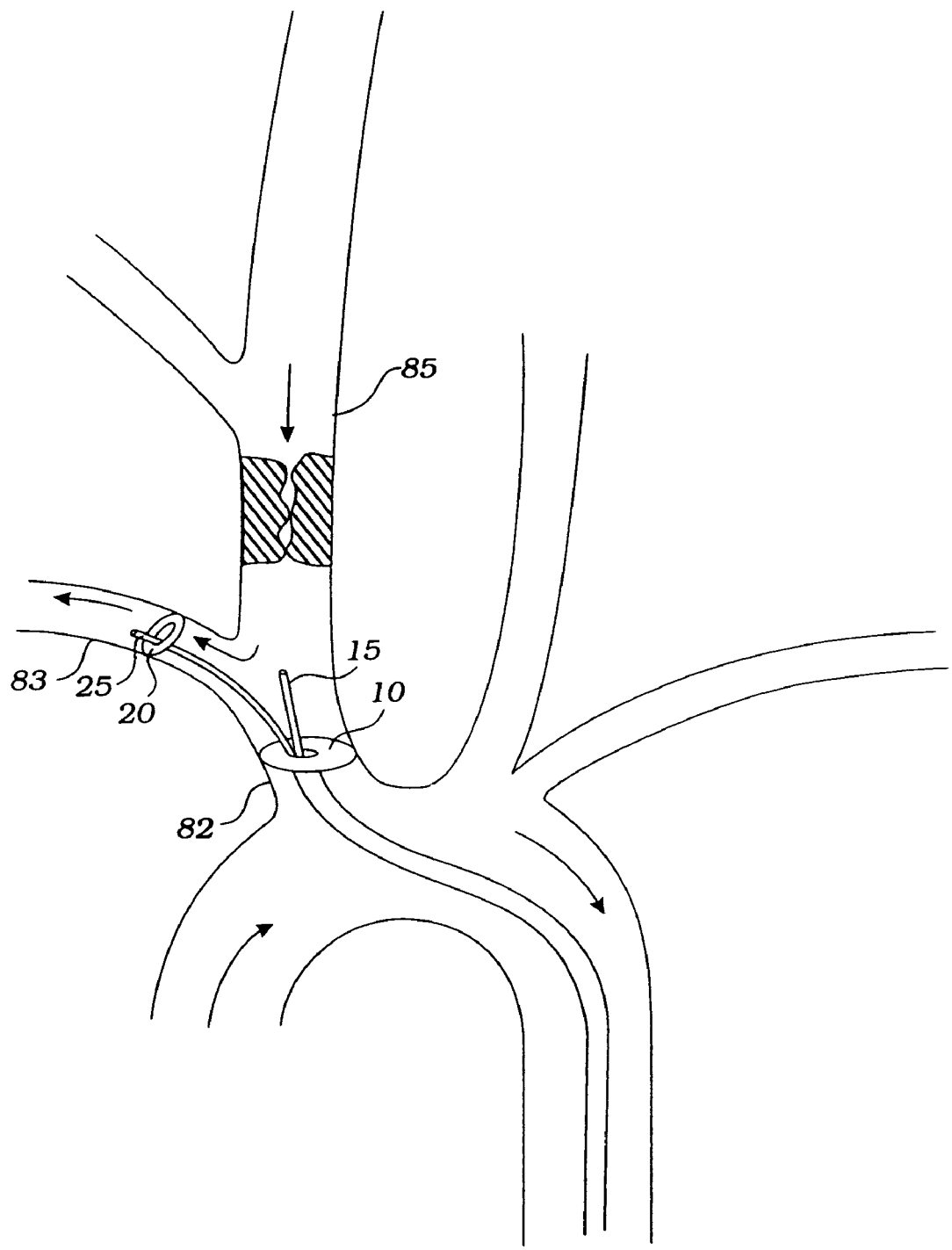
FIG. 8 depicts the device of FIG. 5 inserted in the right brachiocephalic artery and the right subclavian artery to increase the pressure gradient between the right common carotid artery and the right subclavian artery.

If flow reversal does not occur due to insufficient blood flow from contralateral circulation to the CCA, i.e., an insufficient pressure gradient between the CCA and the subclavian artery, the device of FIG. 5 is useful to increase the pressure gradient between the CCA and the subclavian artery as shown in FIG. 8. In use, the distal end of the device is inserted into right brachiocephalic artery 82. The separation between occluder 10 and constrictor 20 is adjusted to ensure proper placement in the respective arteries. Preferably, occluder 10 is slowly expanded through inflation lumen 11 to constrict brachiocephalic artery 82, causing progressive decline of pressure in the subclavian artery. The pressure in the subclavian artery distal to the constrictor and the pressure in the subclavian artery distal to the occluder can be measured, respectively, by manometers 25 and 15. At a critically low pressure in the distal brachiocephalic artery, blood flow in CCA 85 reverses toward the brachiocephalic artery and into the subclavian artery. The reversal of blood flow down the CCA and up the subclavian artery can be verified fluoroscopically with dye. If flow reversal does not occur due to insufficient pressure gradient between the CCA and the subclavian artery, constrictor 20 is gradually expanded to further reduce the pressure in the subclavian artery to create a more favorable pressure gradient between the CCA and the subclavian artery to reverse blood flow into the subclavian artery.

Figure 9:
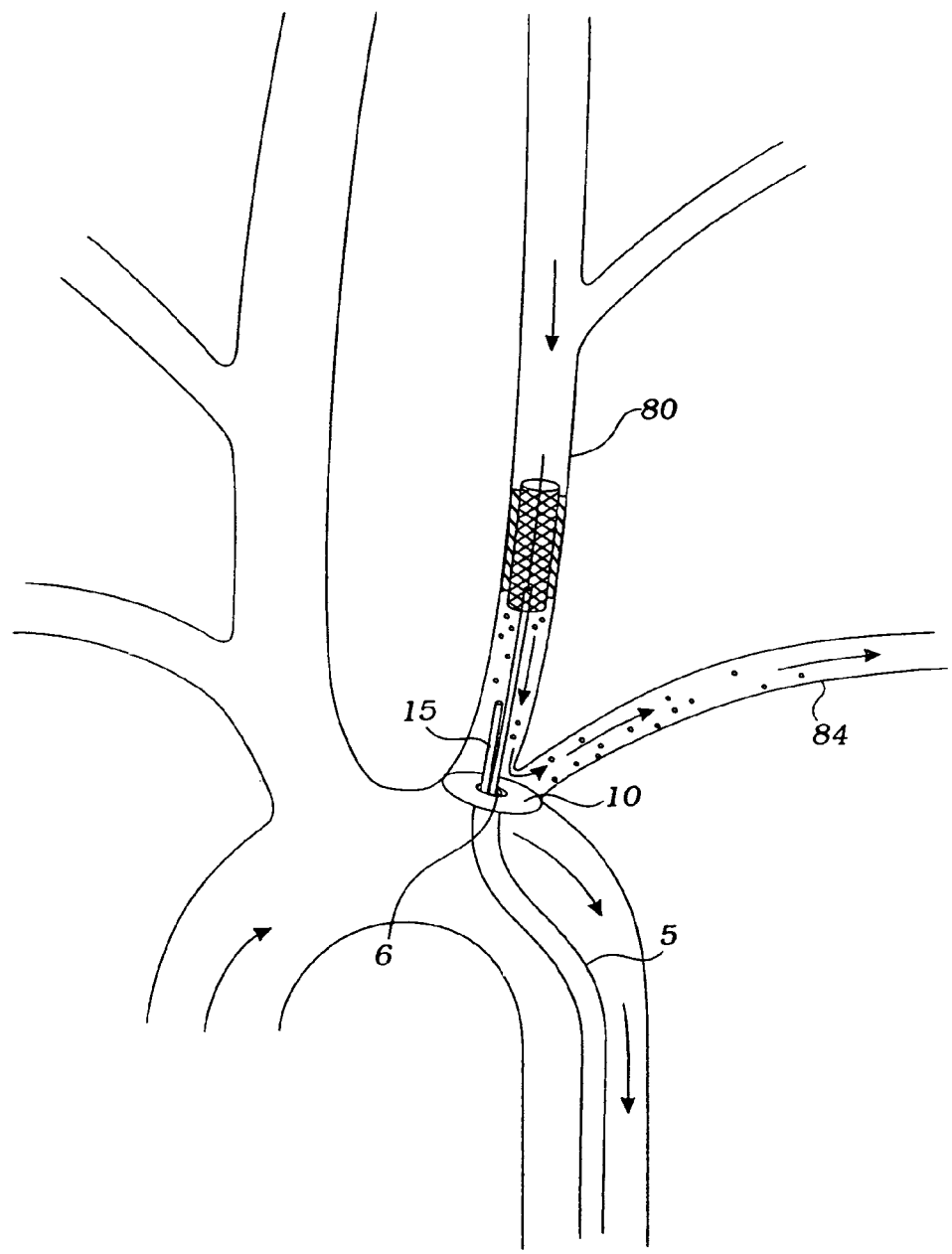
FIG. 9 depicts the constricting member of the device of FIG. 3B constricting the inlets of the left common carotid artery and the left subclavian artery.

In treating an occluding lesion in the left common carotid artery, the device of FIG. 3B is shown inserted in the inlets of left CCA 80 and left subclavian artery 84 as depicted in FIG. 9. Occluding member 10 is expanded to limit blood flow from the aorta into the CCA and the subclavian artery. After blood flow reverses from left CCA 80 and into left subclavian artery 84, a therapeutic instrument, such as a stent is inserted through lumen 5 and port 6. The stent is shown deployed over the atheromatous lesion in CCA 80, thereby compressing the lesion and enlarging the lumenal diameter. With reversal of blood flow from the CCA to the subclavian artery, distal embolization of debris generated by compression of the atheromatous lesion to the intracranial cerebral arteries is avoided, thereby minimizing risk of ischemic stroke.

Figure 11:
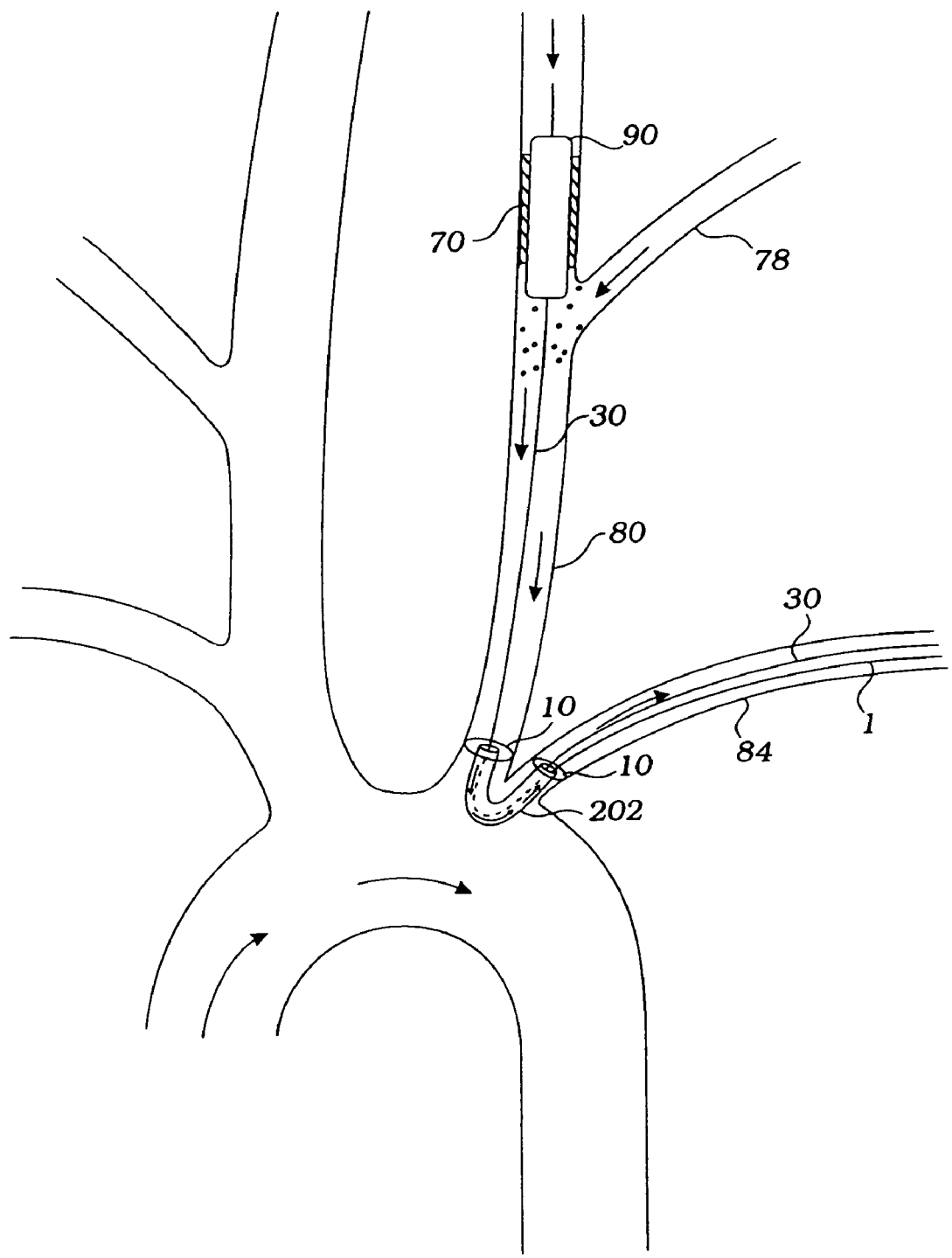
FIG. 11 depicts an occlusion catheter capable of bridging between the left common carotid artery and the left subclavian artery.
Figure 11A:
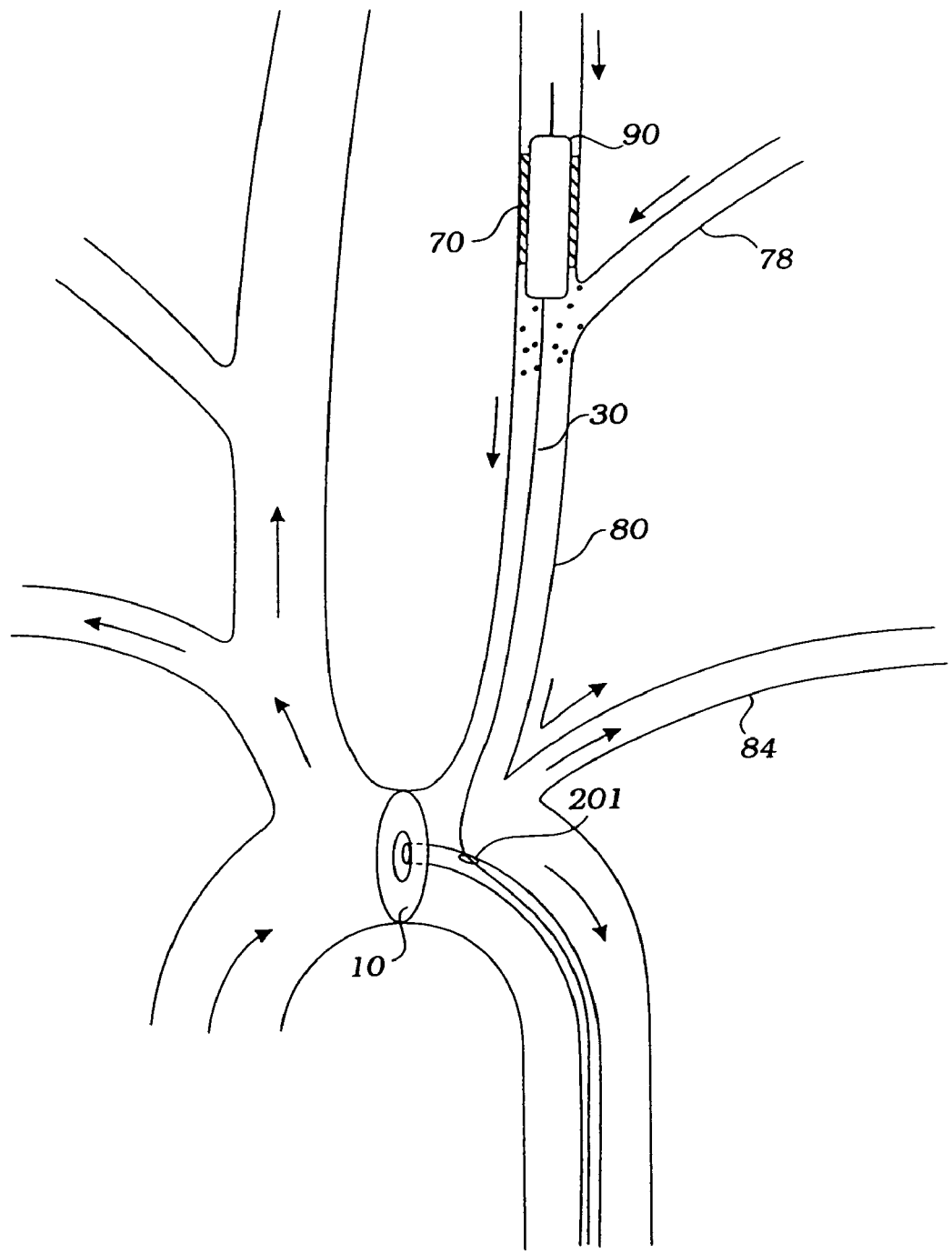
FIG. 11A depicts an aortic constriction catheter capable of causing flow reversal down the left CCA.

FIG. 11 depicts an alternative embodiment wherein first and second occluding members 10 are expanded to occlude each of the left CCA and left subclavian artery. Flow reversal from left CCA 80 to left subclavian 84 is established through tubular member 202 mounted at the distal end of catheter 1. Interventional catheter is deployed through tubular member 202 into left CCA 80. In certain embodiments, a third balloon (not shown) will be used to block the flow of emboli into the left vertebral artery. Flow reversal from left CCA 80 to left subclavian 84 can also be accomplished by placing constricting member 10 in the aorta between the brachiocephalic artery and the left CCA as shown in FIG. 11 A.

Figure 10:
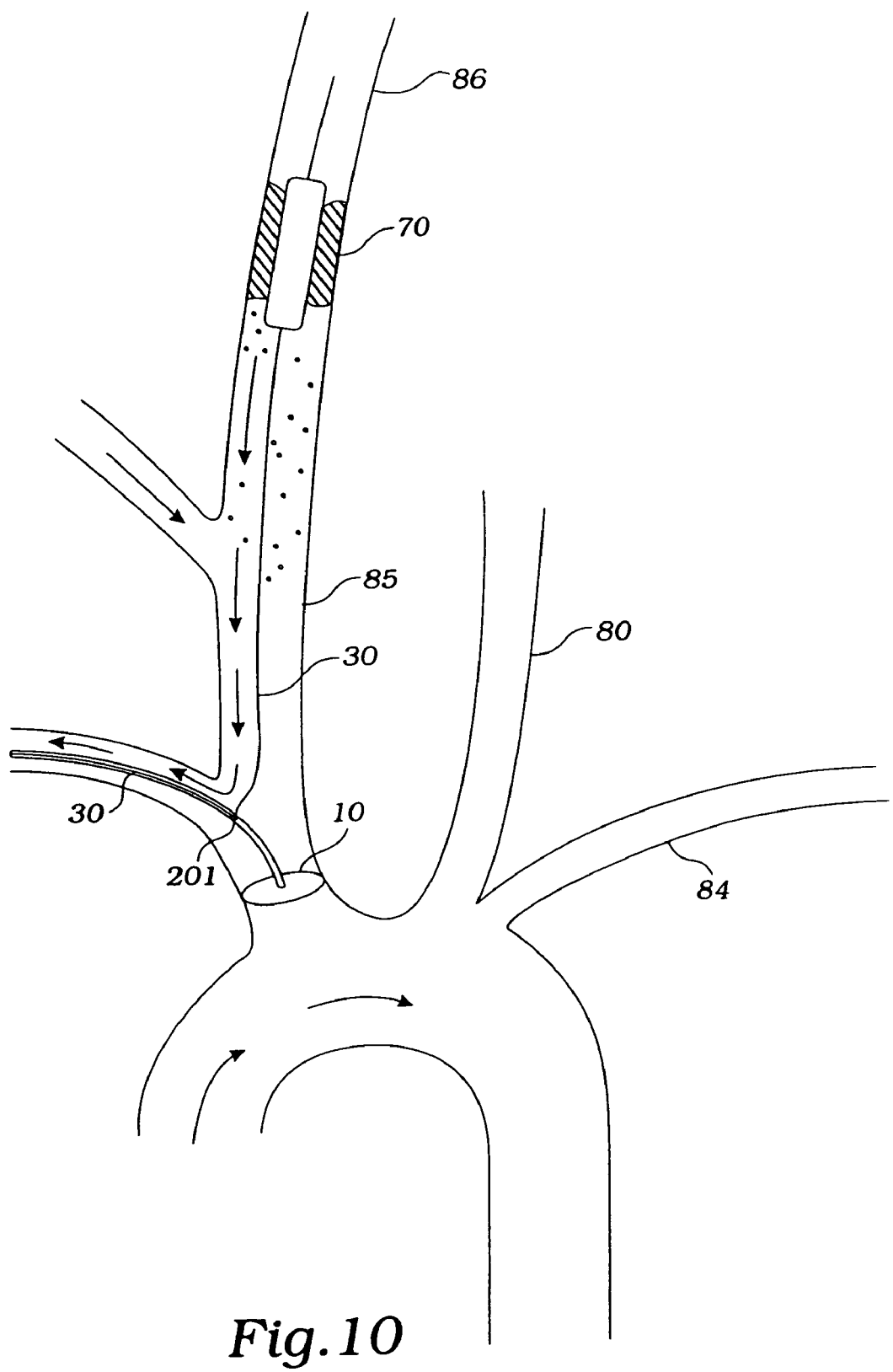
FIG. 10 depicts an occlusion catheter suitable for introduction through the right subclavian artery.

FIG. 10 depicts the use of a catheter adapted for retrograde insertion into the right subclavian artery. Occlusion member 10 is expanded in the right brachiocephalic artery to establish flow reversal from the right CCA to the right subclavian. Catheter 30, here an angioplasty catheter, is advanced through port 201 to access stenosis 70 in right ICA 86.

Figure 12:
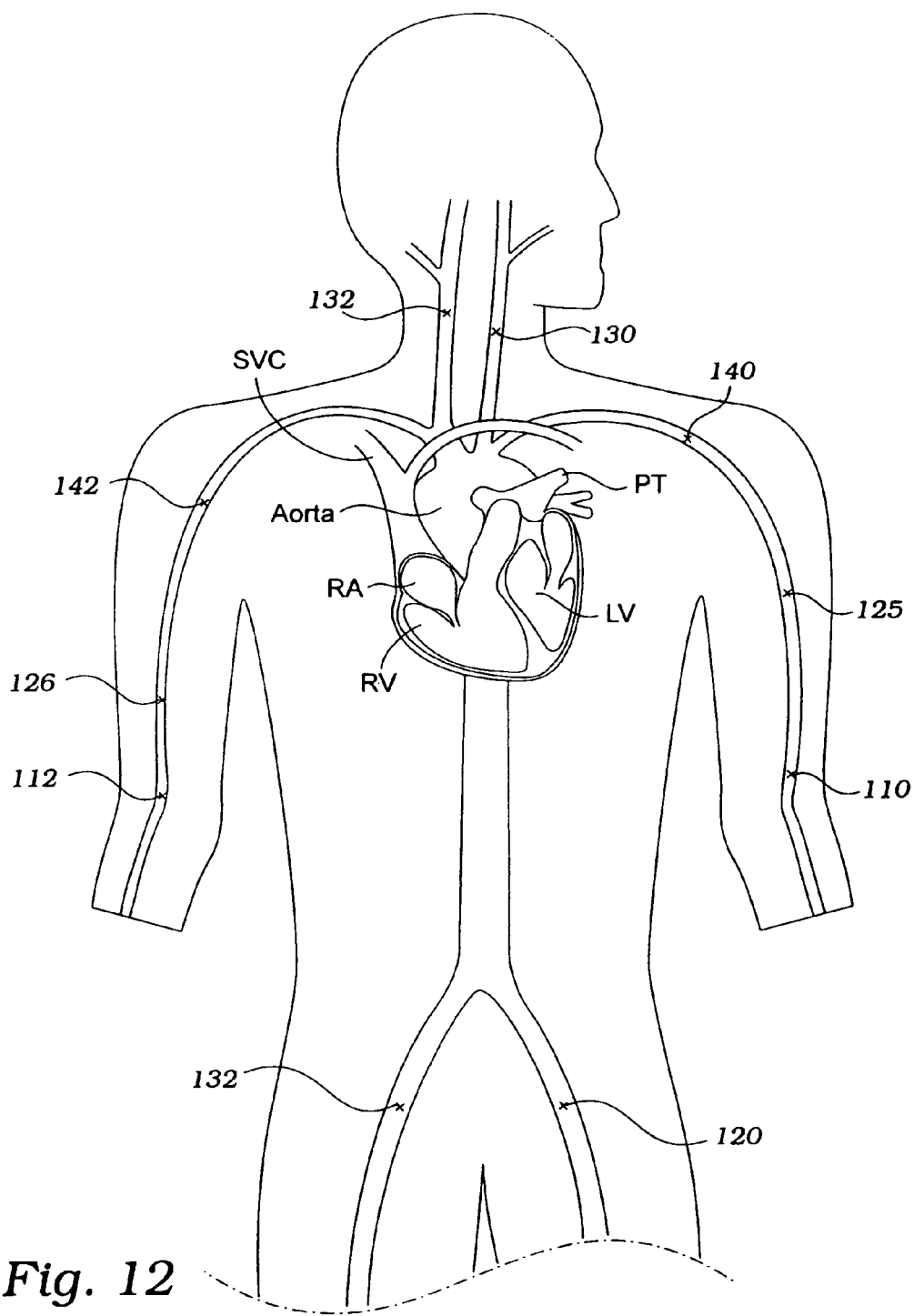
FIG. 12 depicts incision sites on various peripheral arteries for the insertion of the medical devices.

FIG. 12 depicts different sites of entry for the devices disclosed herein. An incision can be made on a peripheral artery, such as right femoral artery 122, left femoral artery 120, right brachial artery 112, left brachial artery 110, right axillary artery 126, left axillary artery 115, right subclavian artery 142, or left subclavian artery 140.

The length of catheter will generally be between 10 and 200 centimeters, preferably approximately between 30 and 150 centimeters. The inner diameter of the catheter lumen will generally be between 0.2 and 0.8 centimeters, preferably approximately between 0.3 and 0.5 centimeters. The diameter of the expanded occluder will generally be between 0.3 and 2 centimeters, preferably approximately 0.5 and 1.0 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. For example, the devices and features depicted in any depicted embodiment can be used in any other depicted embodiment.

What is claimed is:

1. A method for reversing flow in a carotid artery, comprising the steps of:
   providing a catheter having a proximal end, a distal end, and an elongate tubular member at the distal end, the elongate tubular member having a first constricting member at a proximal end and a second constricting member at a distal end;
   inserting the first constricting member into a left common carotid artery;
   inserting the second constricting member into a left subclavian artery; and
   expanding the first and second constricting members, wherein blood flow in the left common carotid artery is reversed to pass through the elongate tubular member and into the left subclavian artery.

2. The method of claim 1, further comprising the step of advancing a therapeutic instrument into the left common carotid artery, a left internal carotid artery, or a left external carotid artery to reduce a lesion.

3. The method of claim 2, wherein the therapeutic instrument is a stent catheter.

4. The method of claim 2, wherein the catheter has a lumen adapted to pass the therapeutic instrument.

5. The method of claim 4, wherein the catheter has a side opening adapted to pass the therapeutic instrument.

6. The method of claim 1, further comprising the step of infusing an angiographic dye to confirm the reversal of blood flow.

7. The method of claim 1, wherein the distal end of the catheter further comprises a radiopaque marker.

8. The method of claim 1, wherein the first constricting member is a balloon.

9. The method of claim 8, wherein the first constricting member is a toroidal balloon.

10. The method of claim 1, wherein the second constricting member is a balloon.

11. The method of claim 10, wherein the second constricting member is a toroidal balloon.

12. The method of claim 1, further comprising the step of inserting a third balloon to block the flow of emboli into a left vertebral artery.

* * * * *